United States Patent [19]
Laughlin

[11] Patent Number: 5,922,333
[45] Date of Patent: Jul. 13, 1999

[54] SYSTEM FOR AUTOMATICALLY COATING THE HUMAN BODY

[75] Inventor: Thomas J. Laughlin, Grapevine, Tex.

[73] Assignee: Laughlin Products, Inc., Grapevine, Tex.

[21] Appl. No.: 08/946,764

[22] Filed: Oct. 8, 1997

Related U.S. Application Data

[60] Provisional application No. 60/039,489, Feb. 28, 1997, and provisional application No. 60/052,498, Jul. 14, 1997.

[51] Int. Cl.$^6$ .............................. A61K 6/00; A61K 7/00; A61K 7/42; A61K 31/74
[52] U.S. Cl. ..................... 424/401; 424/59; 424/78.02; 424/78.03; 424/78.06
[58] Field of Search ................. 424/59, 78.02, 424/78.03, 78.06, 401, 62, 405, 63, 404; 426/72; 514/847, 906, 919, 886, 887

[56] References Cited

U.S. PATENT DOCUMENTS

| | | |
|---|---|---|
| 3,932,151 | 1/1976 | Lau ............................................ 55/229 |
| 4,231,289 | 11/1980 | Domicent ............................ 98/115 SB |
| 4,832,943 | 5/1989 | Grollier et al. ............................ 424/59 |
| 5,089,269 | 2/1992 | Noda et al. .............................. 424/456 |
| 5,102,660 | 4/1992 | Forestier et al. ......................... 424/401 |
| 5,153,174 | 10/1992 | Band et al. ................................. 514/12 |
| 5,268,166 | 12/1993 | Barnett et al. .............................. 424/47 |

FOREIGN PATENT DOCUMENTS

WO 94/12146  6/1994  WIPO ............................ A61K 7/021

OTHER PUBLICATIONS

Non–Carcinogenicity of Dihydroxyacetone by Skin Painting, Frank J. Akin & Edward Marlowe, Journal of Environmental Pathology and Toxicology, 5:No. 5, pp. 349–351, 1984.

Color Additive: Dihydroxyacetone, Federal Register, 38: No. 148, p. 20615, Aug. 2, 1973.

Theory & Practice of Artificial Tanning Literature & Patent Survey, E. Futterer, Cosmetics and perfumes, 88:No. 8, pp. 31–33, 1973.

Persistence of Skin Color and Fluorescence after Treatment with Dihydroxyacetone, J. A. Johnson & R. M. Fusaro, Dermatology 188: pp. 247, 1994.

Formulating Effective Self–Tanners with DHA, T. Kurz, Cosmetics and Toiletries, 109: No. 11, pp. 55–60, 1994.

Dihydroxyacetone–containing sunless or self–tanning lotions, Stanley B. Levy, Journal of the American Academy of Dermatology, 27:No. 6, pp. 989–993, 1992.

*Spray Application Processes,* Binks Training Division, TD49–2R–4, Aug. 1995.

*Primary Examiner*—Thurman K. Page
*Assistant Examiner*—Sharon Howard
*Attorney, Agent, or Firm*—Michael A. O'Neil

[57] ABSTRACT

In a system for coating human skin, a chemical composition, such as a cosmetic or medical formulation, is uniformly coated over the entire body or selected parts of the body of the person being coated. The system includes atomization of the coating composition, containment of the atomized spray, and residual recovery which together yield a novel method for applying chemical compositions.

40 Claims, 4 Drawing Sheets

SELECT COATING COMPOSITION

↓

ATOMIZE COMPOSITION

↓

CONTAIN ATOMIZED COMPOSITION

↓

DIRECT ATOMIZED COMPOSITION ONTO SKIN

↓

CAPTURE RESIDUAL COMPOSITION

SYSTEM FOR AUTOMATICALLY COATING THE HUMAN BODY

RELATED APPLICATIONS

This application claims priority from Provisional Application Ser. No. 60/039,489 filed on Feb. 28, 1997, and No. 60/052,498 filed on Jul. 14, 1997.

TECHNICAL FIELD

The present invention relates generally to systems for automatically coating the human body or selected parts thereof with predetermined fluids. More particularly, the invention relates to an automated self-tanning system.

BACKGROUND OF THE INVENTION

The application of various fluids to all or selected parts of the human body has been known literally for centuries. However, despite the long standing and wide spread practice of coating the human body with various fluids, there has never been a successful way of automatically coating the human body. Therefore, prior to the present invention, it has been necessary to apply fluids to the body manually.

Manual application of fluids to the human body results in numerous disadvantages. First, it is almost impossible to uniformly coat the human body with fluids using manual application techniques. This is true even in the case of fluids that are provided in aerosol or spray form because such fluids must be rubbed in after application. Second, the application of fluids to certain parts of the human body, for example, the back, require the availability of an assistant in order that proper manual application can be attempted.

The foregoing difficulties are particularly apparent in the case of artificial tanning processes. Artificial tanning has been known for more than 40 years, with artificial tanning products appearing on the U.S. market as early as 1959. The two key types of tanning processes are by colorants and bronzers.

Tanning by colorants is based on the color reaction which occurs between components of the skin and the colorant. The most commonly used chemical for artificial tanning is dihydroxyacetone (DHA). It is widely used in commercial artificial tanning products, and is recognized as safe and effective by the U.S. Food and Drug Administration (FDA). DHA reacts solely with the stratum corneum. It interacts with amines, peptides and free amino acids to generate a Maillard reaction. The resulting products are cyclic and linear polymers that have a yellow or brown color.

Two common bronzers are juglone and lawsone. Both are naphthoquinones. When applied to skin, lawsone produces an orange hue and juglone produces a greenish-brown tan. They are sometimes used in combination with DHA to modify the color or hue of the tan or to intensify the color.

Numerous forms of artificial tanning products are now on the market. They include:
- lotions,
- creams,
- gels,
- oils,
- sprays.

These products are mixtures of a chemically-active skin colorant or a bronzer with combinations of the following:
- moisturizers,
- preservatives,
- antimicrobials,
- thickeners,
- solvents,
- emulsifiers,
- fragrances,
- surfactants,
- stabilizers,
- sun-screens,
- pH adjusters
- anti-caking agents,
- ingredients to alter the color reaction.

Users of these products often experience significant problems associated with the current methods for applying artificial tanning formations to skin. These problems include the following.

If not properly dried, the formulation will streak or form blotches with time. The net result is a very non-uniform tan, with light or dark streaks or blotches.

Certain parts of the body will stain more intensely when the formulation is spread manually. This differential staining is due to enhance absorption of certain skin tissue and the tendency of certain tissue to retain more formulation. The result is that as the formulation is being spread manually, certain tissue absorb or trap more formulation (e.g., the wrinkles in the elbows and knees and the dense tissue in the palms).

Most products designed for manual application require components such as thickeners and polymers, which often inhibit the efficacy of DHA.

Current formulations typically take about 20 minutes to dry to the touch, and about 1 hour before not transferring from skin to textiles.

Application of artificial tanning products is additionally complicated by the tendency of these formulations to stain materials containing amine molecules, including certain fabrics, certain types of carpet, and certain wall coverings and paint.

In spite of all of these problems, artificial tanning is becoming increasingly popular. It is apparent that a need exists for a superior application system which solves the foregoing problems.

There is also a need for a superior applications system for many other applications, including but not limited to:
- self-tanning formulations,
- sunscreens,
- suntan lotions,
- tanning accelerators,
- sunburn treatments,
- insect repellants,
- skin toners,
- skin bleaches,
- skin lighteners,
- anti-microbial compositions,
- moisturizers,
- exfoliants,
- nutriments or vitamins,
- massage aides,
- muscle relaxants,
- skin treatment agents,
- burn treatment agents,
- decontamination agents, cosmetics, wrinkle treatments or removers.

There are specific and significant problems with the manual coating of each of these products. The artificial tanning application provides a good illustration of the types of problems normally encountered when manually coating these products. Artificial tanning is also one of the most demanding applications in that uniformity of the coating is critical to assure uniform tanning.

SUMMARY OF THE INVENTION

The present invention comprises a system for automatically coating the human body, including a method of and apparatus for uniformly and rapidly coating all or selected parts of the human body. The system includes apparatus which atomizes (also referred to as aerosolization, nebulization, mist generation, fog generation or spray generation) a chemical composition and deposits it uniformly over all or selected parts of the human body. It is not necessary for the individual receiving the treatment nor anyone else to manually apply any of the formulation. Also, a containment system is provided which restrains and collects residue from the application process. The system can optionally recycle the materials used.

There are several major advantages resulting from the use of the invention:

Uniform application minimizes or eliminates streaking,

No assistant is required for applying the composition,

The entire skin surface receives the same exposure to the composition, so the uniformly of the coating is greatly enhanced over manual application, The optimal formulation for atomization is very simple, and does not require the addition of components which may inhibit the efficacy of the applied material, The application time can be as quick as a few seconds, and complete drying can occur in just a few minutes,
- The containment system drastically reduces the unwanted environmental impact,
- Multiple applications can be used to better control the amount of material applied per unit area, and additional substances can be applied in separate applications.

REFERENCES

U.S. patent documents 3,932,151 1/1976 Lau 55/229

4,231,289 11/1980 Domicent 98/115

5,268,166 12/1993 Barnett 424/047

Foreign patent documents

WO 94/12146 6/1994 PCT Int'l Appl.

Other publications

Akins, F. J. and Marlowe, E., "Non-Carcinogenicity of Dihydroxyacetone by Skin Painting," Journal of Environmental Pathology and Toxicology, 5: No. 5, pp. 349–351 (1984).

Federal Register, "Color Additive Dihydroxyacetone" 38: No. 148, p. 21615, Aug. 2, 1973.

Futterer, E., "Theory and Practice of Artificial Tanning: Literature and Patent Survey," Cosmetics and Perfumes, 88: No. 8, pp. 31–33 (1973).

Johnson, J. A. and Fusaro, R. M., "Persistence of Skin Color and Fluorescence after Treatment with Dihydroxyacetone," Dermatology 188: pp. 247 (1994).

Kurz, T., "Formulating Effective Self-Tanners with DHA," Cosmetics and Toiletries, 109: No. 11, starting p. 55 (1994).

Levy, S. B., "Dihydroxyacetone-Containing Sunless or Self-tanning Lotions," Journal of the American Academy of Dermatology, 27: No. 6, pp. 989–993 (1992).

"Spray Application Processes," BINKS training brochure TD49-2R-4, August, 1995, BINKS Manufacturing Company, Franklin, Ill.

BRIEF DESCRIPTION OF THE DRAWINGS

A more complete understanding of the invention may be had by reference to the following Detailed Description when taken in conjunction with accompanied Drawings, wherein:

FIG. 1 is a flow chart illustrating the invention;

FIG. 2 is a diagrammatic illustration of the system for automatically coating the human body of the present invention comprising the minimum requirements thereof;

FIG. 3 is an illustration similar to FIG. 2 wherein the system of the present invention is further provided with containment apparatus;

FIG. 4 is an illustration similar to FIG. 3 wherein the system of the present invention is further provided with an air ventilation apparatus;

FIG. 5 is an illustration similar to FIG. 4 wherein the system of the present invention is further provided with collection apparatus for residual spray;

FIG. 6 is an illustration similar to FIG. 5 wherein the system of the present invention is further provided with apparatus to effect rotation of the human body being coated;

FIG. 7 is an illustration similar to FIG. 6 wherein the system of the present invention is further provided with multiple discharge nozzles; and FIG. 8 is an illustration similar to FIG. 5 wherein the system of the present invention is adapted to the coating of a selected part of the human body.

DETAILED DESCRIPTION OF THE INVENTION

Referring now to the Drawings, and particularly to FIG. 1, the system for automatically coating the human body of the present invention may comprise an automated coating system for numerous types of formulations, including but not limited to the application of:

self-tanning formulations, sunscreens, suntan lotions, tanning accelerators, sun-burn treatments, insect repellants, skin toners, skin bleaches, skin lighteners, anti-microbial compositions, moisturizers, exfoliants, nutriments or vitamins, massage aides, muscle relaxants, skin treatment agents, burn treatment agents, decontamination agents, cosmetics, wrinkle treatments or removers.

The first component of such a system is the chemical composition. The suitability of a composition for coating is strongly influenced by its viscosity, with the preferred viscosity being close to that of water (1 centipoise). Compositions with viscosities in the 1 to 10 centipoise range generally atomize well, and viscosities in the 10 to 100 range can be atomized, but the resulting spray is not as fine. Higher viscosities can be atomized, and will work, but the spray is not as fine. Most currently marketed compositions of the aforementioned applications can be made suitable for atomization either as is or with appropriate dilution.

By way of example, a more detailed description of functional compositions for use in practice of the invention will be based on artificial tanning compositions. Four such compositions are given in Compositions 1, 2, 3 and 4. Individuals skilled in this art can create other compositions.

| Ingredient | % |
|---|---|
| COMPOSITION 1 | |
| Dihydroxyacetone | 3 |
| Water | 97 |
| COMPOSITION 2 | |
| Dihydroxyacetone | 3.0 |
| Denatured Ethanol | 20.0 |
| Water | 77.0 |
| COMPOSITION 3 | |
| Dihydroxyacetone | 12.0 |
| Denature Ethanol | 20.0 |
| Water | 68.0 |
| COMPOSITION 4 | |
| Dihydroxyacetone | 10.0 |
| Commercial Sunless-Tanning Lotion | 15.0 |
| Water | 75.0 |

By way of example, suitable commercial preparations include Coppertone® Oil-Free Sunless Tanner (Schering-Plough, Memphis, Tenn.), Neutrogena® Glow Sunless Tanning Lotion for Face and Body (Neutrogena, Los Angeles, Calif.), and Kroger® Sunless Tanning Cream (Kroger, Cincinnati, Ohio).

Compositions 1, 2 and 3 are greatly simplified versions of the formulations now on the market or reported in the past. This simplification is possible due to the use of the present invention for applying compositions to skin. These simplified compositions have several advantages over more complex formulations, including:

- faster drying,
- less potential inhibition of DHA efficacy,
- less potential for irritation from chemical components (because there are fewer components),
- less residue on the skin,
- less expensive,
- more environmentally friendly.

Composition 4 illustrates how a commercial formulation not particularly well suited for atomization can be diluted, effectively atomized and uniformly coated on human skin. Similar dilutions of products representing the other aforementioned applications can be effectively atomized and coated on human skin.

A preferred colorant is DHA. DHA is available from Rona (Hawthorne, N.Y.). It is effective, safe, and approved by the FDA for this application. The preferred DHA concentration is 0.5% to 20%, with a more preferred range of 3.0% to 15.0%, and a most preferred range of 5% to 12%. Numerous other colorants can also be used. Those agents include, but are not limited to:

- crotonaldehyde
- pyruvaldehyde
- glycolaldehyde
- glutaraldehyde
- otho-phthaldehyde
- sorbose
- fructose
- erythrulose
- methylvinylketone
- food coloring Various dyes and UV blocking agents can be covalently linked to the colorant or can be mixed into the composition with the colorant.

Bronzers can also be used in combination with or as an alternative to DHA. Bronzers which can be used include, but are not limited to, lawsone and juglone. Combinations of DHA and bronzers can also be used, and can be used to modify the resulting color (hue) and intensity of the tan. The preferred range for lawsone and juglone is 0.5% to 10.0% with the more preferred range of 1.0% to 5.0%. There is no pH adjustment required for these compositions, although the pH can be adjusted to alter the hue of the resulting tan and to alter the dihydroxyacetone stability. The optimal tanning occurs with DHA at a pH of below 6.0, preferably with the solution at pH 3.0 to 4.0. Unbuffered DHA has a pH of about 5.5. The pH on the surface of human skin is also about 5.5. Nonetheless, these formulations can be used over a wide pH range, and buffers or pH adjusters can be added.

Alcohol can be added to the composition to accelerate the rate of drying. Denatured ethanol (USP grade, commodity chemical) works well in this capacity. The preferred range for alcohol concentration is from 1.0% to 50.0%, with a more preferred range from 10.0% to 30.0%, and a most preferred concentration of 20.0%.

Other potential additives include:

- moisturizers,
- preservatives,
- antimicrobials,
- thickeners,
- solvents,
- emulsifiers,
- fragrances,
- stabilizers,
- sun-screens,
- surfactants,
- pH adjusters,
- anti-caking agents,
- ingredients to alter the color reaction.

It typically requires about 100 ml of a 5.0% DHA composition to obtain a medium to dark tan over an entire adult body (about 2 square meters of skin). A single application of about 150 ml of a 12% dihydroxyacetone composition over an entire adult human body will result in a very dark tan. The exact amount of dihydroxyacetone required depends on the skin type and intensity of tan desired. The tan can last for about 2 to 7 days, but usually lasts for 3 to 4 days. Multiple applications will darken the tan.

The second component of the invention is the atomization of the composition. The required atomization can be obtained by a host of ways, most of which involve passing the composition through an orifice under pressure. Methods now used to atomize solutions include the use of the following systems:

air atomization
  siphon feed
  gravity feed
  pressure feed
    internal atomization
    external atomization
    low pressure low volume
    high volume low pressure
airless atomization
  pressurized through small orifices
air-assisted
air-assisted heated
electrostatic
  using charged particles
  heated charged particles
  high speed rotational atomizers
ultrasonic These forms of atomization are the basis for most methods of producing atomized sprays, including misting and nebulization.

Using a single airless sprayer with a tip orifice of 0.6 mm, with a circular spray pattern of 12 inches at 12 inches from the tip, and with a flow rate of approximately 400 ml/min. the entire body (excluding the bottom of the feet) of an average-sized person can be coated with solution in 5 to 15 seconds. In practice, the underside of the feet usually get slightly tanned also from exposure to small quantities of residual artificial tanning composition on the floor of application area The use of a single airless sprayer to apply a composition to human skin is illustrated in FIG. 2. In this figure and subsequent figures, 11 designates the orifice for atomization of the composition, 12 designates the atomized spray, and 13 designates the subject being sprayed. In this configuration, an operator must direct the flow of the spray. The configuration illustrated in FIG. 2 would also work for any of the other atomization methods aforementioned, and for any of the applications aforementioned. The preferred atomization method is the pressure-fee air-atomization system, with an internal or external atomization configuration.

For a person to be coated as illustrated in FIG. 2 with an artificial tanning composition (or any composition of the applications aforementioned), several precautions should be taken. First, the person should hold their breath during the application and during the time required for the spray to clear. If this process is done in an open area, the coating should take about 5 to 15 seconds and the clearing of residues should take 1 to 10 seconds. Thus, the person would need to hold their breath for 6 to 25 seconds. Alternatively, they could wear a filter over their mouth, have a filter inside of their mouth, or use a breathing tube. They can also wear nose plugs or filters. Second, the eyes should be protected even though most of these formulations are not likely to injure the eye. The simplest and most effective protection is to keep the eyes closed. Goggles or patches also work well, although they leave uncoated areas that must be subsequently coated manually. Next, precautions need to be taken if one wants to avoid the exposure of scalp hair. Scalp hair can be protected with a shower cap or any other similar protective covering impervious to the coating compositions. Also, hair can be coated with a water insoluble material such as petroleum jelly. Similar protection can be used to protect hair on any other parts of the body. Next, if atomization is from a single source, it is recommended that the person being coated turn while being coated, or that the coating apparatus be moved around the person being coated, or there be a combination of these movements. Finally, care must be taken that the nozzle remain at least several inches from the person being coated to prevent any possible injection of composition into the person. Generally, spray injection occurs at pressures greater than 500 psi with the person actually contacting the atomization orifice. The pressures here are less than 80 psi, and more typically 10 to 40 psi, and the person being coated should be a foot or more from the orifice.

The issue of what to wear during coating is usually of great concern to the person being coated. In the case of coating with artificial tanning solution, the selection of what to wear is a matter of preference for the person being coated. The subject can be coated nude, with underwear, with a bikini or a bathing suit, or with some form of pasties covering their private parts.

The third component of the invention is containment of the spray. Containment is illustrated in FIG. 3. In this figure and subsequent figures, 14 and 15 designate side panels and 16 and 17 designate the top and bottom panels, respectively. This type of containment is similar to the containment of spray paint using paint booths in automobile refinishing. Alternatively, spray containment can be obtained using electrostatic forces, where the atomized spray is charged and the residual charged spray is removed by activating charged collection plates. Of course, precautions must be taken so that the person being sprayed and the operator are isolated from the charged plates.

Containment of the spray is very important for several reasons. These reasons include but are not limited to:

- reducing waste,
- avoiding spray getting onto and staining items in the immediate surroundings,
- facilitating capture and recovery processes,
- better control of air flow,
- better control of temperature and humidity.

This type containment facilitates the use of this invention in enclosed areas such as stores or medical facilities.

Control of air and spray flow is very important to the quality of the skin coating. It is highly preferable to have an exhaust fan drawing the spray towards the person being coated, and the residual composition out of the booth. In FIG. 4 is shown the addition of an exhaust fan 18. The fan offers several significant advantages to the invention. These advantages include but are not limited to:

- better control of air flow
- shorter exposure to residue spray, requiring less time to hold breath or breathe through filter or air line
- faster drying of the coated composition on skin
- better quality coating The fan 18 should have a flow of 10 to 5000 cubic feet per minute per square foot of opening, preferably 50 to 1000 cubic feet per minute per square foot, and most preferably 100 to 400 cubic feet per minute per square foot. At flow rates of below 100 cubic feet per minute per square foot, the air movement is sufficient to guide the atomized spray through the containment area At flow rates of 100 to 400 cubic feet per minute per square foot, the atomized spray is being actively drawn through the containment area and the application and drying process is enhanced. At rates above 400 cubic feet per minute per square foot, the atomized spray is being accelerated and the exhaust flow plays a much more prominent role in the application process. The flow rate of the air through the containment area is therefore a major parameter which can be varied to modify the characteristics of the coating of the artificial tanning composition to the skin. The drying time for the composition deposited on skin is also effected by flow rate, with drying time decreasing as flow rates increase. At rates above 100 cubic feet per minute per square foot, the drying time (to the point of no transfer to other surfaces upon contact) is less than 5 minutes.

At any flow rate above 10 cubic feet per minute per square foot, the residual atomized spray is completely removed from the containment area within one second This rapid removal is important to minimize the time the person being tanned is exposed to spray and has the potential to inhale this spray. In the absence of this air flow, the residual spray lingers in the area for several minutes, and traces can be detected hours later. This vigorous flow also protects any individuals or operators near the atomizing orifices from back spray.

Figure 1:
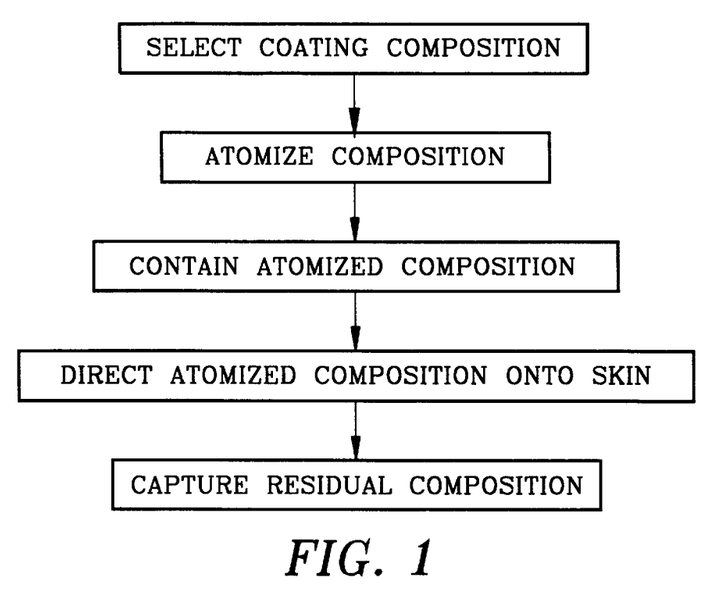
Figure 2:
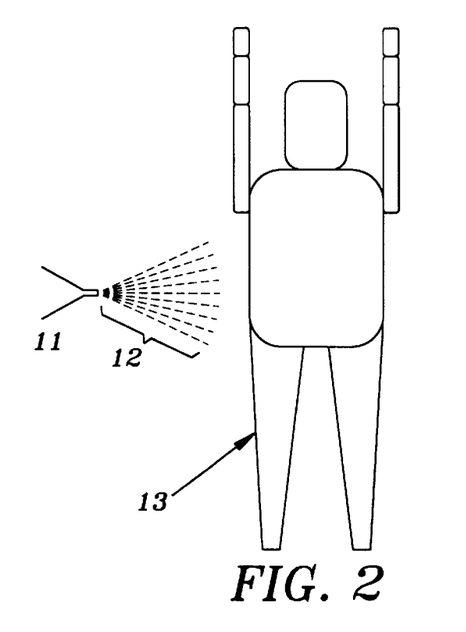
Figure 3:
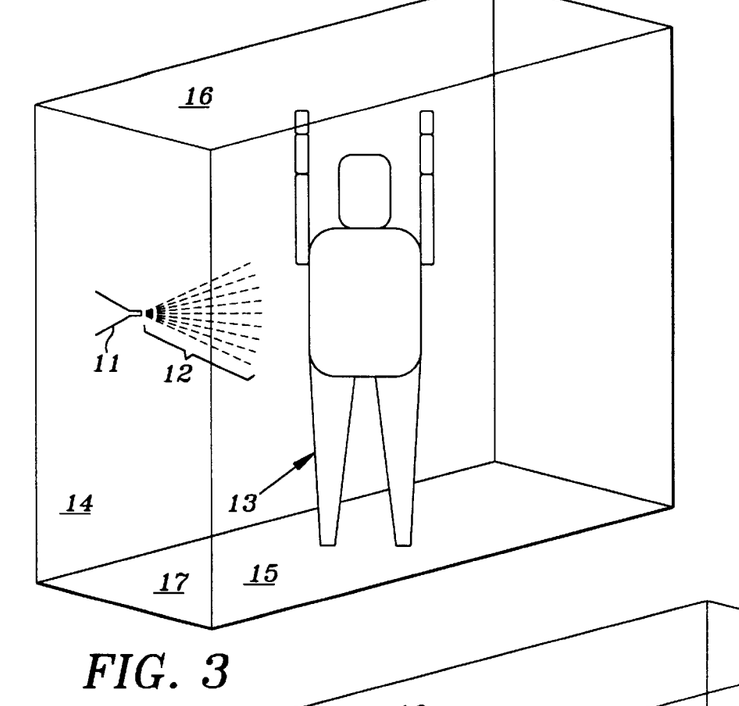
Figure 4:
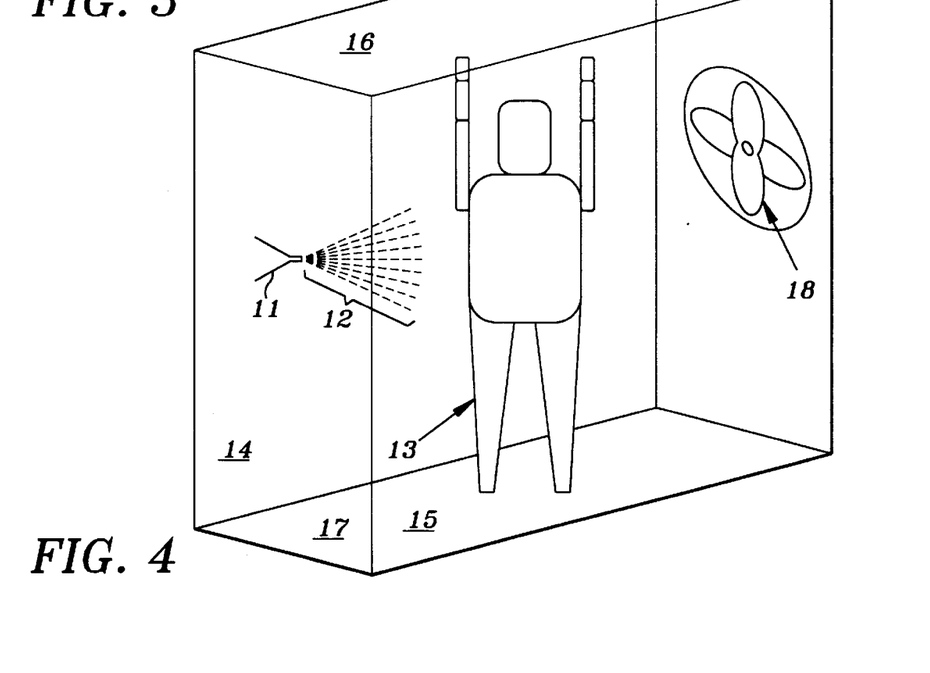
Figures 5, 6:
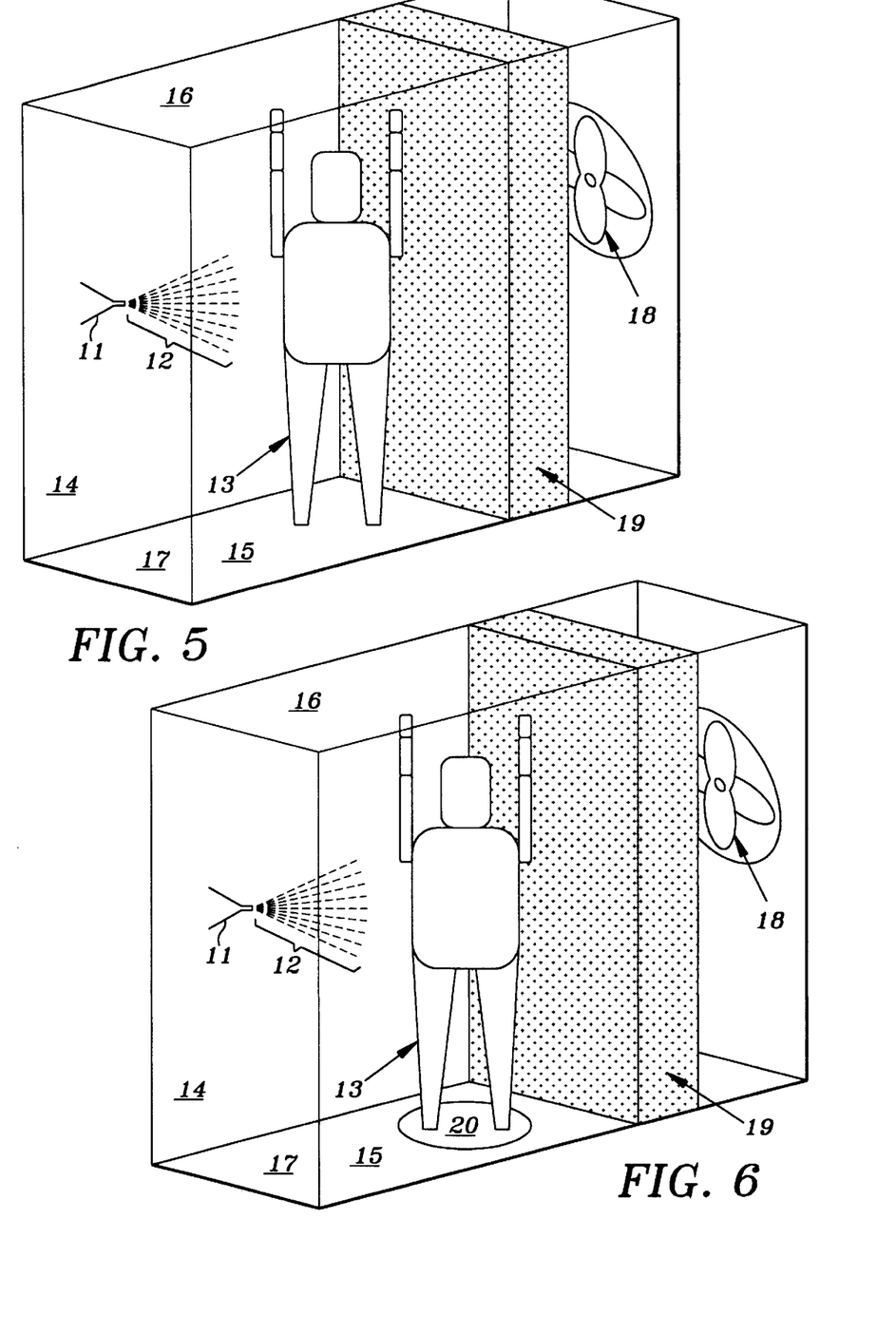

The final element of this invention is recovery, or filtering, of residual composition. This feature greatly enhances the utility of the invention because it allows the system to be self-contained in an indoor environment and promotes a more environmentally friendly process. Without a recovery system, there is a potential for the exhausted residue to stain anything it contacts. Also, there could be an accumulation of residue with time. One configuration of the recovery system is shown in FIG. 5. In this figure and subsequent figures, the recovery system or filter is denoted as 19. Recovery of both particulates and solvents is possible. Potential filters include a high-efficiency filter such as Binks' (Franklin Park, Ill.) Paint Pockets or Columbus Industries' (Ashville, Ohio) High-Capacity Supra Mini-Mesh, a form of a carbon filter, a water-wash filter, or an exchange-type resin. The efficiency of particulate and solvent removal should be greater than 99%. As an alternative to high-efficiency filtering, the spray residuals could be vented to the outside environment.

Figure 7:
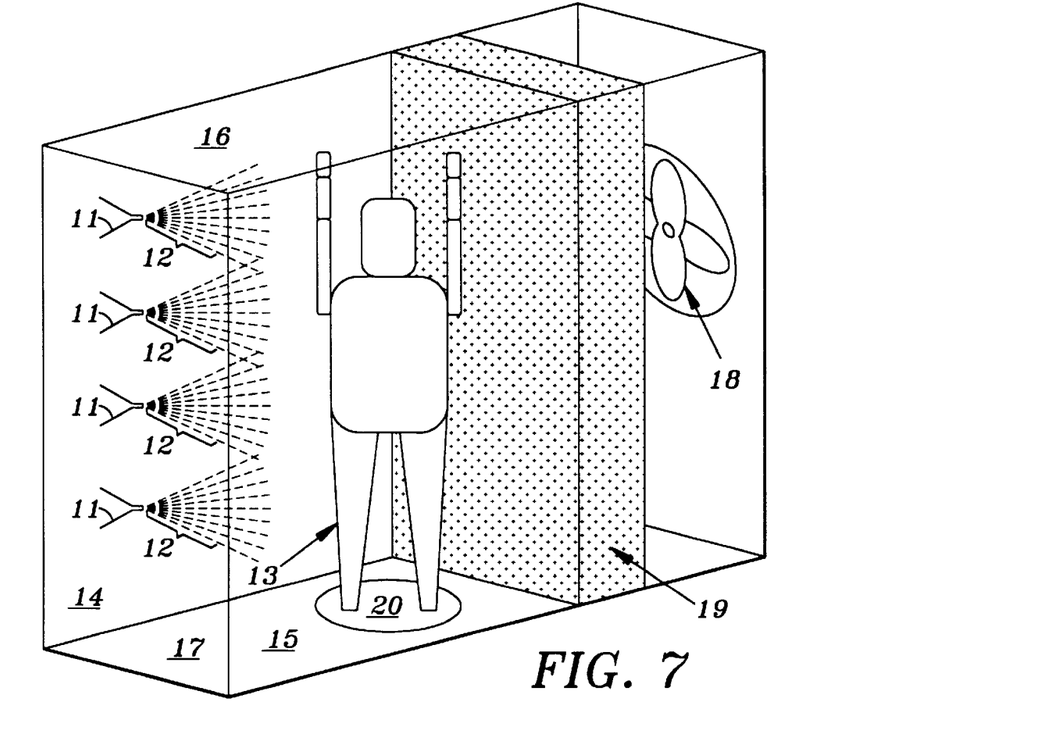

Additional features adding to the utility of the invention are shown in FIG. 6 and FIG. 7. In FIG. 6 there is shown the addition of a motorized turntable 20. This turntable 20 will rotate the person being coated, eliminating rotation by the individual as a possible source of error or problems. It also is a major convenience for the person being coated. The preferred rate of rotation is in the range of 1 to 60 rpm, with a more preferred range of 5 to 20 rpm, with a most preferred rate of rotation of 12 rpm.

In FIG. 7 there is shown the use of multiple atomizing orifices. The use of multiple orifices facilitates the automation of this process, and reduces operator effort and potential error. It also reduces the time required to fully coat an individual. The typical round spray pattern is about 12 inches wide at 8 to 12 inches from the orifices, so a preferred spacing of multiple orifices will be 8 to 12 inches apart, but could be positioned from 1 to 48 inches apart. Fan patterns from wide-angle nozzles at 18 inches are typically 24 inches long and 9 inches wide. Using the preferred configuration, an individual can be coated in 5 seconds or less. In FIG. 7, the orifices are aligned in a vertical pattern. The coverage of more area at one time could also be obtained by rapidly moving one or more orifices along a track or by rapidly altering the angle of the orifice. Other patterns are possible, including combinations of vertical and horizontally aligned orifices. Orifices could also be aligned radially, with the subject being sprayed with orifices aligned from 0 to 360°. Another alignment is a horizontal ring containing orifices that surround the body. By vertically raising and lowering the horizontal ring, the entire body or selected parts of the body could be coated.

In an open environment, such as a beach or a park, a modified version of configuration illustrated in FIG. 7 could be used to rapidly coat an individual. It would even be possible to have a walk-through coating system. An atomized spray could be produced from multiple nozzles arranged in a single line (as shown in FIG. 7), in two single lines facing one another and about 36 to about 48 inches apart, or multiple lines of nozzles. The preferred configuration is multiple lines, with 4 lines being adequate. The atomized spray results in an area of intense atomized solution, which would coat an individual standing in that area. The residual spray would then be dissipated into the surrounding environment. A fan could be used to accelerate the removal of the residuals from the coating area.

Figure 8:
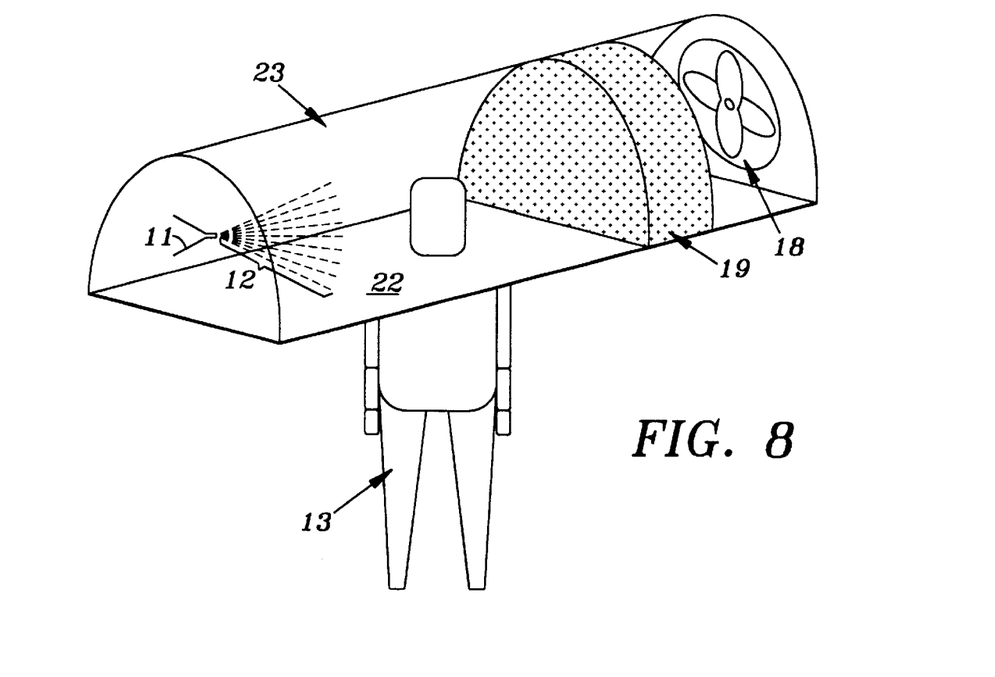

FIG. 8 illustrates how the system of the present invention can be used to tan a selected part of the body. In this case, just the face is being tanned. In this figure the bottom panel of the apparatus 22 contains an opening through which one can insert his or her head. The top panel 23 is arched. The high-efficiency filter is 19. The fan and back panel is 15. Alternately, the setup as shown in FIGS. 2–7 could be used to tan only a select part of the body by protecting the area not desired to be tanned with appropriate barrier apparel or by screens between the atomized spray and the regions of the skin not to be coated. The barrier apparel could be any material impervious to the atomized coating composition. For example, materials appropriate for use with the aforementioned coating compositions include vinyl, polyurethane, and latex rubber. The screens can be sheets composed of any material impervious to the atomized artificial tanning compositions, including most metals or plastics. A preferred screening material is foam with an impervious aluminum foil backing. The foam is aligned with the backing away from the atomizing orifice. The foam is preferred because it absorbs much of the atomized spray, reducing back deflection.

Although preferred embodiments of the invention are illustrated in the Drawings and described in the Detailed Description, it will be understood that the invention is not limited to the embodiments disclosed, but is capable of numerous modifications and rearrangements of parts and elements without departing from the spirit of the invention.

What is claimed is:

1. A method of coating human skin including the steps of:
   a. providing a predetermined human skin coating composition;
   b. atomizing the human skin tanning composition at a predetermined rate;
   c. directing the atomized composition onto at least predetermined portions of the body of the person to be coated;
   d. containing the atomized spray; and
   e. capturing the portion of the atomized spray not deposited on the body of the person being coated.

2. The method for artificially coating human skin according to claim 1 wherein the predetermined human skin coating composition comprises dihydroxyacetone in a concentration of between about 0.5% and about 20%, with the balance of the composition comprising water.

3. The method for artificially coating human skin according to claim 1 wherein the predetermined human skin coating composition comprises a naphthoquinone in a concentration of between about 0.5% and about 10%, with the balance of the composition comprising water.

4. The method of artificially coating human skin according to claim 1 wherein the predetermined human skin coating composition comprises dihydroxyacetone in a concentration of between about 0.5% and about 20%, a naphthoquinone in a concentration of between about 0.5% and about 10%, with the balance of the composition comprising water.

5. The method of artificially coating human skin according to claim 2 wherein the predetermined human skin coating composition further includes an alcohol in a concentration of between about 1% and about 50%.

6. The method of artificially coating human skin according to claim 3 wherein the predetermined human skin coating composition further includes an alcohol in a concentration of between about 1% and about 50%.

7. The method of artificially coating human skin according to claim 4 wherein the predetermined human skin coating composition further includes an alcohol in a concentration of between about 1% and about 50%.

8. The method of artificially coating human skin according to claim 2 wherein the predetermined human skin coating composition further includes a predetermined artificial tanning cream or lotion in a concentration of between about 5% and about 20%.

9. The method for coating human skin according to claim 1 wherein the coating composition is a predetermined sunscreen composition.

10. The method for coating human skin according to claim 1 wherein the coating composition is a predetermined suntanning composition.

11. The method for coating human skin according to claim 1 wherein the coating composition is a predetermined tanning accelerator composition.

12. The method for coating human skin according to claim 1 wherein the coating composition is a predetermined sunburn treatment composition.

13. The method for coating human skin according to claim 1 wherein the coating composition is a predetermined insect repellant composition.

14. The method for coating human skin according to claim 1 wherein the coating composition is a predetermined skin toner composition.

15. The method for coating human skin according to claim 1 wherein the coating composition is a predetermined skin bleach composition.

16. The method for coating human skin according to claim 1 wherein the coating composition is a predetermined skin lightening composition.

17. The method for coating human skin according to claim 1 wherein the coating composition is a predetermined anti-microbial composition.

18. The method for coating human skin according to claim 1 wherein the coating composition is a predetermined moisturizer composition.

19. The method for coating human skin according to claim 1 wherein the coating composition is a predetermined exfoliant composition.

20. The method for coating human skin according to claim 1 wherein the coating composition is a predetermined nutriment and vitamin composition.

21. The method for coating human skin according to claim 1 wherein the coating composition is a predetermined massaging aide composition.

22. The method for coating human skin according to claim 1 wherein the coating composition is a predetermined muscle relaxant composition.

23. The method for coating human skin according to claim 1 wherein the coating composition is a predetermined medicated skin treatment composition.

24. The method for coating human skin according to claim 1 wherein the coating composition is a predetermined burn treatment composition.

25. The method for coating human skin according to claim 1 wherein the coating composition is a predetermined decontamination composition.

26. The method for coating human skin according to claim 1 wherein the coating composition is a predetermined cosmetic composition.

27. The method for coating human skin according to claim 1 wherein the coating composition is a predetermined wrinkle treatment composition.

28. The method of coating human skin according to claim 1 wherein the step of atomizing the coating composition comprises forcing the composition through a small diameter orifice and producing an atomized spray.

29. The method of coating human skin according to claim 1 wherein the step of directing the atomized spray of coating composition onto the body of the person to be coated includes the step of directing a flow of air containing the atomized composition pass the body of the person being coated at a rate of between about 10 cubic feet a minute and about 5000 cubic feet a minute per square foot.

30. The method of coating human skin according to claim 1 further includes the step of rotating the body of the person to be coated around a vertical axis during the application of the atomized coating composition.

31. The method of coating human skin according to claim 1 wherein the step of atomizing the coating composition is further characterized by forcing the predetermined coating composition through a plurality of small diameter orifices.

32. A method of coating human skin according to claim 1 wherein the steps for containing the atomized spray and for capturing the portion of atomized spray not deposited on the body of the person being coated are carried out by dissipating the uncoated atomized spray into the surrounding environment.

33. The method of coating human skin according to claim 1 wherein the step of capturing the portion of the atomized spray not deposited on the body of the person being coated is accomplished by the use of electrostatic plates which draw the charged residual spray from the area where the person is being coated to one or more adjacent areas containing the charged electrostatic plates.

34. A method of coating human skin including the steps of;
   a. providing a predetermined human skin coating composition;
   b. atomizing the human skin tanning composition at a predetermined rate;
   c. directing the atomized human skin tanning composition onto at least predetermined portions of the body of a person to be tanned;
   d. containing the atomized spray; and
   e. capturing the portion of the atomized spray which is not deposited on the body of the person being tanned.

35. The method for artificially coating human skin according to claim 34 wherein the predetermined human skin coating composition comprises dihydroxyacetone in a concentration of between about 0.5% and about 20%, with the balance of the composition comprising water.

36. The method of artificially coating human skin according to claim 34 wherein the predetermined human skin coating composition comprises a naphthoquinone in a concentration of between about 0.5% and about 10%, with the balance of the composition comprising water.

37. The method of artificially coating human skin according to claim 34 wherein the predetermined human skin coating composition comprises dihydroxyacetone in a concentration of between about 0.5% and about 20%, a naphthoquinone in a concentration of between about 0.5% and about 10%, with the balance of the composition comprising water.

38. The method of artificially coating human skin according to claim 35 wherein the predetermined human skin coating composition further includes an alcohol in a concentration of between about 1% and about 50%.

39. The method of artificially coating human skin according to claim 36 wherein the predetermined human skin coating composition further includes an alcohol in a concentration of between about 1% and about 50%.

40. The method of artificially coating human skin according to claim 37 wherein the predetermined human skin coating composition further includes an alcohol in a concentration of between about 1% and about 50%.

* * * * *

US005922333C1

(12) EX PARTE REEXAMINATION CERTIFICATE (5184th)
United States Patent
Laughlin (10) Number: US 5,922,333 C1
(45) Certificate Issued: Aug. 16, 2005

(54) SYSTEM FOR AUTOMATICALLY COATING THE HUMAN BODY

(75) Inventor: Thomas J. Laughlin, Grapevine, TX (US)

(73) Assignee: Laughlin Products, Inc., Grapevine, TX (US)

Reexamination Request:
No. 90/006,547, Feb. 12, 2003
No. 90/006,663, Jun. 10, 2003
No. 90/006,711, Jul. 14, 2003

Reexamination Certificate for:
Patent No.: 5,922,333
Issued: Jul. 13, 1999
Appl. No.: 08/946,764
Filed: Oct. 8, 1997

Related U.S. Application Data
(60) Provisional application No. 60/039,489, filed on Feb. 28, 1997, and provisional application No. 60/052,498, filed on Jul. 14, 1997.

(51) Int. Cl.$^7$ ................................................. A61K 7/42
(52) U.S. Cl. .................... 424/59; 424/401; 424/78.02; 424/78.03; 424/78
(58) Field of Search .................................. 424/59, 401

(56) References Cited

U.S. PATENT DOCUMENTS

| | | |
|---|---|---|
| 870,766 A | 11/1907 | Eaton |
| 1,262,638 A | 4/1918 | Class |
| 1,982,509 A | 11/1934 | Frank |
| 2,700,384 A | 1/1955 | Ivory |
| 2,949,403 A | 8/1960 | Andreadis |
| 3,060,097 A | 10/1962 | Fellows |
| 3,272,713 A | 9/1966 | Runge |
| 3,856,934 A | 12/1974 | Kligman |
| 3,868,950 A | 3/1975 | Kato |
| 3,920,808 A | 11/1975 | Fusaro |

(Continued)

FOREIGN PATENT DOCUMENTS

| | | |
|---|---|---|
| BE | 814319 | 8/1974 |
| DE | 3605807 | 2/1986 |
| DE | G9319158.8 | 3/1994 |
| FR | 814319 | 8/1974 |
| FR | 2725362 | 10/1994 |
| WO | WO94/12146 | 6/1994 |

OTHER PUBLICATIONS

Fusaro et al. (1966), Sunlight protection in normal skin, *Archives of Dermatology*, vol. 93, pp. 106–111 (Jan. 1966).
Fusaro et al. (1970). Erythropoietic protoporphyria IV. Protection from sunlight. *Br. Med. J.*, vol. 1, pp. 730–731.
Fusaro et al. (1971). Sunlight protection in patients with chlorpromazine light sensitivity. *Int. J. Dermatol*, vol. 10, pp. 198–200.
Fusaro et al. (1972). Protection against light sensitivity with dihydroxyacetone/naphthoquinone. *Int. J. Dermato,*. vol. 11, pp. 67–70.
Fusaro et al. (1974). Photoprotection of patients sensitive to short and/or long ultraviolet light with dihydroxyacetone/naphthoquinone. *Dermatologica*, vol. 148, pp. 224–227.
Johnson et al. (1973). Protection against long ultraviolet light with dihydroxyacetone/naphthoquinone. *Dermatologica*, vol. 47, pp. 104–108.
Non–Carcinogenicity of Dihydroxyaceton by Skin Painting, Frank J. Akin and Edward Marlowe, Journal of Environments Pathology and Toxicology, 5: No. 5, pp. 349–351, 1984.
Color Additives: Dihydroxyaceton, Federal Register, 38: No. 148, p. 20615, Aug. 2, 1973.
Formulating Effective Self–Tanners with DHA, T. Kurz, Cosmetics and Toiletries, 109: No. 11, pp. 55–60, 1994.

(Continued)

*Primary Examiner*—Jyothsna Venkat (57) ABSTRACT

In a system for coating human skin, a chemical composition, such as a cosmetic or medical formulation, is uniformly coated over the entire body or selected parts of the body of the person being coated. The system includes atomization of the coating composition, containment of the atomized spray, and residual recovery which together yield a novel method for applying chemical compositions.

U.S. PATENT DOCUMENTS

| | | | |
|---|---|---|---|
| 3,932,151 A | 1/1976 | Lau | 55/229 |
| 4,231,289 A | 11/1980 | Domicent | 98/115 |
| 4,453,941 A | 6/1984 | Jacobs | 424/59 |
| 4,749,130 A | 6/1988 | Utzinger | |
| 4,826,681 A | 5/1989 | Jacquet et al. | 424/613 |
| 4,832,943 A | 5/1989 | Grollier et al. | 424/59 |
| 4,874,412 A | 10/1989 | Nowack | 55/385.1 |
| 5,089,269 A | 2/1992 | Noda et al. | 424/456 |
| 5,102,660 A | 4/1992 | Forestier et al. | 424/401 |
| 5,153,174 A | 10/1992 | Band et al. | 514/12 |
| 5,232,688 A | 8/1993 | Ziegler | |
| 5,268,166 A | 12/1993 | Barnett et al. | 424/47 |
| 5,273,214 A | 12/1993 | Huffstutler | 239/279 |
| 5,302,378 A | 4/1994 | Crotty et al. | |
| 5,456,211 A | 10/1995 | Stevenson | 119/157 |
| 5,460,192 A | 10/1995 | McClain | |
| 5,494,674 A | 2/1996 | Barnett et al. | 424/401 |
| 5,512,278 A | 4/1996 | Mundschenk | 424/78.06 |
| 5,545,399 A | 8/1996 | Lee et al. | 424/59 |
| 5,567,420 A * | 10/1996 | McEleney et al. | 424/60 |
| 5,603,923 A | 2/1997 | Robinson et al. | 424/60 |
| 5,662,890 A | 9/1997 | Punto et al. | |
| 5,664,593 A | 9/1997 | McClain | |
| 5,700,452 A | 12/1997 | Deckner et al. | 424/59 |
| 5,773,014 A | 6/1998 | Perrier et al. | 424/401 |
| 5,880,314 A | 3/1999 | Sinomiya et al. | 568/729 |
| 6,214,322 B1 | 4/2001 | Castro et al. | 424/59 |
| 6,231,837 B1 | 5/2001 | Stroud et al. | 424/59 |

OTHER PUBLICATIONS

Dihydroxyaceton–containing sunless or self–tanning lotions, Stanley B. Levy, Journal of the AmericanAcademy of Dermatology, 27: No. 6, pp. 989–993, 1992.

Spray Application Processes, Binks Training Division, TD49–2R–4, Aug. 1995.

Theory & Practice of Artificial Tanning Literature & Patent Survey, E. Futterer, Cosmetics and perfunes, 88: No. 8, pp. 31–33, 1973.

Persistence of Skin Color and Fluorescence after Treatment with Dihydroxyaceton, J.A. Johnson & R.M. Fusaro, Dermatology 188: p. 247, 1994.

* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 9–27 and 35–40 are cancelled.

Claims 1–8 and 28–34 are determined to be patentable as amended.

New claims 41–49 are added and determined to be patentable.

1. A method of coating human skin *with an artificial tanning composition* including the steps of:
   a. *providing a booth for receiving the entire body including the head of a person to be coated;*
   [a.] *b.* providing a [predetermined human skin coating composition] *human skin artificial tanning composition*;
   [b.] *c.* atomizing the human skin *artificial* tanning composition at a predetermined rate;
   [c.] *d.* directing the atomized *human skin artificial tanning* composition onto [at least predetermined portions of the] *substantially the entire* body *including the head* of the person to be coated, *the entire body including the head being located in the booth during the coating thereof*;
   [d.] *e.* containing the atomized spray *comprising the atomized human skin artificial tanning composition within the booth*; and
   [e.] *f.* capturing the portion of the atomized spray *comprising the atomized human skin artificial tanning composition* not deposited on the body of the person being coated.

2. The method [for artificially coating human skin] according to claim 1 wherein the [predetermined] human skin [coating] *artificial tanning* composition comprises *a sprayable liquid including* dihydroxyacetone in a concentration of between about 0.5% and about 20%, with the balance of the composition comprising water.

3. The method [for artificially coating human skin] according to claim 1 wherein the [predetermined] human skin [coating] *artificial tanning* composition comprises *a sprayable liquid including* a naphthoquinone in a concentration of between about 0.5% and about 10%, with the balance of the composition comprising water.

4. The method [of artificially coating human skin] according to claim 1 wherein the [predetermined] human skin [coating] *artifical tanning* composition comprises *a sprayable liquid including* dihydroxyacetone in a concentration of between about 0.5% and about 20%, a naphthoquinone in a concentration of between about 0.5% and about 10%, with the balance of the composition comprising water.

5. The method [of artificially coating human skin] according to claim [2] *1* wherein the [predetermined] human skin [coating] *artifical tanning* composition [further includes an alcohol in a concentration of between about 1% and about 50%] *comprises a sprayable liquid including dihydroxyacetone in a concentration of between about 0.5% and about 20%, an alcohol in a concentration of between about 1% and about 50%, with the balance of the composition comprising water*.

6. The method [of artificially coating human skin] according to claim [3] *1* wherein the [predetermined] human skin [coating] *artificial tanning* composition [further includes an alcohol in a concentration of between about 1% and about 50%] *comprises a sprayable liquid including a naphthoquinone in a concentration of between about 0.5% and about 10%, an alcohol in a concentration of between about 1% and about 50%, with the balance of the composition comprising water*.

7. The method [of artificially coating human skin] according to claim [4] *1* wherein the [predetermined] human skin [coating] *artificial tanning* composition [further includes an alcohol in a concentration of between about 1% and about 50%] *comprises a sprayable liquid including dihydroxyacetone in a concentration of between about 0.5% and about 20%, a naphthoquinone in a concentration of between about 0.5% and about 10%, an alcohol in a concentration of between about 1% and about 50%, with the balance of the composition comprising water*.

8. The method [of artificially coating human skin] according to claim [2] *1* wherein the [predetermined] human skin [coating] *artificial tanning* composition [further includes a predetermined artificial tanning cream or lotion in a concentration of between about 5% and about 20%] *comprises a sprayable liquid including dihydroxyacetone in a concentration of between about 0.5% and about 20%, a predetermined artificial tanning cream or lotion in a concentration of between about 5% and about 20%, with the balance of the composition comprising water*.

28. The method [of coating human skin] according to claim 1 wherein the step of atomizing the [coating] *human skin artificial tanning* composition comprises forcing the composition through a small diameter orifice and producing an atomized spray.

29. The method [of coating human skin] according to claim 1 wherein the step of directing the atomized [spray of coating] *human skin artificial tanning* composition onto *substantially* the *entire* body of the person to be coated includes the step of directing a flow of air containing the atomized composition [pass] *past* the body *including the head* of the person being coated at a rate of between about 10 cubic feet a minute and about 5000 cubic feet a minute per square foot.

30. The method of coating human skin according to claim 1 further [includes] *including* the step of rotating the body *including the head* of the person to be coated around a vertical axis during the application of the atomized coating composition.

31. The method [of coating human skin] according to claim 1 wherein the step of atomizing the [coating] *human skin artificial tanning* composition is further characterized by forcing the [predetermined coating] *human skin artificial tanning* composition through a plurality of small diameter orifices.

32. [A] *The* method [of coating human skin] according to claim 1 wherein the steps [for] *of* containing the atomized spray and [for] *of* capturing the portion of atomized spray not deposited on the body *including the head* of the person being coated [are carried out by] *include the step of* dissipating [the] uncoated atomized spray into the surrounding environment.

33. The method of coating human skin according to claim 1 wherein the step of capturing the portion of the atomized spray not deposited on the body *including the head* of the person being coated is accomplished by the use of electrostatic plates which draw the charged residual spray from the area where the person is being coated to one or more adjacent areas containing the charged electrostatic plates.

34. A method of coating human skin *with a human skin artificial tanning composition* including the steps of:
   a. providing a booth for receiving the entire body *including the head* of a person to be coated;
   [a.] b. providing a [predetermined human skin coating composition] *human skin artificial tanning composition*;
   c. *providing at least one nozzle within the booth;*
   [b.] d. directing the human skin *artificial* tanning composition through the nozzle and thereby atomizing the human skin *artificial* tanning composition at a predetermined rate;
   e. *moving the nozzle relative to the person to be coated during the atomizing step;*
   [c.] f. directing the atomized human skin *artificial* tanning composition onto [at least predetermined portions of the] *substantially the entire* body *including the head* of a person to be *artificial* tanned, *the entire body including the head being located in the booth during the coating thereof*;
   [d.] g. containing the atomized spray *comprising the atomized human skin artificial tanning composition* within the booth; and
   [e.] h. capturing the portion of the atomized spray *comprising the atomized artificial tanning composition* which is not deposited on the body of the person being [tanned] *coated*.

41. *The method of claim 1, wherein the human skin artificial tanning composition comprises dihydroxyacetone in a concentration of between about 0.5% and about 20%, with the balance of the composition including water.*

42. *A method of coating human skin with an artificial tanning composition including the steps of:*
   a. *providing a booth for receiving a body including the head of a person to be coated;*
   b. *providing a human skin artifical tanning composition;*
   c. *providing a plurality of nozzles;*
   d. *positioning the nozzles in a horizontally spaced apart array within the booth;*
   e. *forcing the human skin artificial tanning composition through the nozzles and thereby atomizing the human skin artificial tanning composition at a predetermined rate;*
   f. *directing the atomized human skin artificial tanning composition onto substantially the entire body including the head of a person to be coated, the entire body including the head being located in the booth during the coating thereof;*
   g. *containing the atomized spray comprising the atomized human skin artificial tanning composition within the booth; and*
   h. *capturing the portion of the atomized spray comprising the atomized human skin artificial tanning composition which is not deposited on the body of the person being coated,*
   *wherein the human skin artificial tanning composition comprises dihydroxyacetone in a concentration of between about 0.5% and about 20%, with the balance of the composition including water.*

43. *A method of coating human skin with an artificial tanning composition including the steps of:*
   a. *providing a booth for receiving a body including the head of a person to be coated;*
   b. *providing a human skin artificial tanning composition;*
   c. *providing a plurality of nozzles;*
   d. *positioning the nozzles in a horizontal array within the booth;*
   e. *forcing the human skin artificial tanning composition through the nozzles and thereby atomizing the human skin artificial tanning composition at a predetermined rate;*
   f. *directing the atomized human skin artificial tanning composition onto substantially the entire body including the head of a person to be coated, the entire body including the head being located in the booth during the coating thereof;*
   g. *moving at least one of the nozzles relative to the body including the head of a being coated during the atomizing step;*
   h. *containing the atomized spray comprising the atomized human skin artificial tanning composition within the booth; and*
   i. *capturing the portion of the atomized spray comprising the atomized human skin artificial tanning composition which is not deposited on the body of the person being coated,*
   *wherein the human skin artificial tanning composition comprises dihydroxyacetone in a concentration of between about 0.5% and about 20%, with the balance of the composition including water.*

44. *A method of coating human skin including the steps of:*
   a. *providing a human skin coating composition comprising an artificial tanning composition;*
   b. *providing a human body including a head;*
   c. *providing a booth;*
   d. *positioning the human body including the head within the booth;*
   e. *atomizing the composition at a predetermined rate;*
   f. *artificially tanning the body by directing the atomized composition onto substantially the entire body including the head;*
   g. *containing the atomized composition within the booth;*
   h. *capturing the atomized composition not coated on the body; and*
   i. *filtering at least a portion of the captured composition and thereby recovering unused human skin artificial tanning composition for disposal.*

45. *The method of claim 1, wherein the atomizing of the human skin artificial tanning composition at a predetermined rate is carried out at a pressure of less than 80 psi.*

46. *The method of claim 2, additionally comprising filtering at least part of the portion of the atomized human skin artificial tanning composition not deposited on the body of the person being coated and thereby recovering the unused human skin artificial tanning composition for disposal.*

47. *The method of claim 5, additionally comprising filtering at least part of the portion of the atomized human skin artificial tanning composition not deposited on the body of the person being coated and thereby recovering unused human skin artificial tanning composition for disposal.*

48. *The method of claim 8, additionally comprising filtering at least part of the portion of the atomized human skin* artificial tanning composition not deposited on the body of the person being coated and thereby recovering unused human skin artificial tanning composition for disposal.

49. The method of claim 29, additionally comprising filtering at least part of the portion of the atomized human skin artificial tanning composition not deposited on the body of the person being coated and thereby recovering unused human skin artificial tanning composition for disposal.

\* \* \* \* \*